United States Patent
Kohn et al.

(10) Patent No.: US 7,521,061 B2
(45) Date of Patent: Apr. 21, 2009

(54) PHARMACEUTICAL FORMULATION FOR REGULATING THE TIMED RELEASE OF BIOLOGICALLY ACTIVE COMPOUNDS BASED ON A POLYMER MATRIX

(75) Inventors: Joachim B. Kohn, South Plainfield, NJ (US); Deborah M. Schachter, Edison, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 10/169,410

(22) PCT Filed: Jan. 2, 2001

(86) PCT No.: PCT/US01/00030

§ 371 (c)(1),
(2), (4) Date: Dec. 9, 2002

(87) PCT Pub. No.: WO01/49249

PCT Pub. Date: Jul. 12, 2001

(65) Prior Publication Data

US 2003/0138488 A1     Jul. 24, 2003

Related U.S. Application Data

(60) Provisional application No. 60/174,137, filed on Dec. 31, 1999.

(51) Int. Cl.
*A61K 9/00* (2006.01)
*A61K 38/00* (2006.01)

(52) U.S. Cl. ............... 424/278.1; 424/400; 435/132; 604/502; 604/175

(58) Field of Classification Search .......... 514/2, 514/772.2, 772.3, 773, 772.4–6, 772.5, 772.6; 424/484, 486
See application file for complete search history.

(56) References Cited

U.S. PATENT DOCUMENTS

| | | | | |
|---|---|---|---|---|
| 4,425,237 A | * | 1/1984 | Abe et al. ............... | 210/692 |
| 4,976,962 A | * | 12/1990 | Bichon et al. ............ | 424/424 |
| 5,317,077 A | | 5/1994 | Kohn et al. ............... | 528/182 |
| 5,670,602 A | | 9/1997 | Kohn et al. ............... | 528/176 |
| 5,877,224 A | * | 3/1999 | Brocchini et al. ........ | 514/772.2 |
| 5,962,471 A | | 10/1999 | Schudok ................... | 514/309 |
| 6,120,491 A | * | 9/2000 | Kohn et al. ............... | 604/502 |
| 6,207,191 B1 | * | 3/2001 | Crison et al. ............. | 424/472 |
| 6,730,349 B2 | * | 5/2004 | Schwarz et al. .......... | 427/2.1 |

FOREIGN PATENT DOCUMENTS

| | | |
|---|---|---|
| WO | WO9719996 | 6/1997 |
| WO | WO9836013 | 8/1998 |
| WO | WO 9924107 A1 * | 5/1999 |
| WO | WO9929758 | 6/1999 |

OTHER PUBLICATIONS

Brocchini, S. (1997). Amino acid derived polymers for use in controlled delivery systems of peptides. Therapeutic Protein and Peptide Formulation and Delivery. Z. Shahrokh et al. eds. Washington, DC, American Chemical Society, 675, pp. 154-166.*
Doerhoefer et al. (2002) The DNA-polymerase inhibiting activity of poly(beta-l-malic acid) in nuclear extract during the cell cycle of Physarum polycephalum. Eur. J. Biochem. vol. 269, No. 4, pp. 1253-1258.*
Phaneuf et al. (1998) Covalent linkage of recombinant hirudin to a novel ionic poly(carbonate) urethane polymer with protein binding sites: determination of surface antithrombin activity. Artif Organs. vol. 22, No. 8, pp. 657-665.*
Phaneuf et al. (1997) Covalent linkage of recombinant hirudin to poly(ethylene terephthalate) (Dacron): creation of a novel antithrombin surface. Biomaterials. vol. 18, No. 10, pp. 755-765.*
Dempsey et al. (1998) Synthesis of a novel small diameter polyurethane vascular graft with reactive binding sites. ASAIO J. vol. 44, No. 5, pp. M506-M510.*
Wikipedia (2007, updated) "Sodium polyarylate", http://en.wikipedia.org/wiki/Sodium_polyarylate, pp. 1-2.*
Lagarce et al. (2002) Oxaliplatin loaded PLAGA microspheres: design of specific release profiles, Internat. J. Pharmaceut., vol. 242, pp. 243-246.*
O'Shea et al., "*Eptifibatide: a potent inhibitor of the platelet receptor integrin, glycoprotein Iib/IIIa,*" Exp. Opin. Invest. Drugs, 8(11), 1893-1905 (1999).
Andrianov et al., "*Protein release form polyphosphazene matrices,*" Adv. Drug Del. Revs., 31, 185-196 (1998).
Cha, Y. and Pitt, C.G., "A One-Week Subdermal Delivery System for L-Methadone Based On Biodegradable Microcapsules," J. Controlled Release, Apr. 1988, 69-78, vol. 7, Elsevier Science Publishers B.V.
Benzine et al., A versatile three-iodine molecular building block leading to new radiopaque polymeric biomaterials, Journal of Biomedical Materials Research, Nov. 1, 1996, pp. 459-466, vol. 32, John Wiley & Sons, Inc., US.

* cited by examiner

*Primary Examiner*—Jon P Weber
*Assistant Examiner*—Samuel W. Liu
(74) *Attorney, Agent, or Firm*—Fox Rothschild LLP

(57) ABSTRACT

A formulation containing a biologically active compound having a structure with hydrogen bonding sites is blended with a polymer having a structure with complementary hydrogen bonding sites, the polymer forming hydrolytic degradation products that promote the release of the biologically active compound from the polymer.

20 Claims, 11 Drawing Sheets

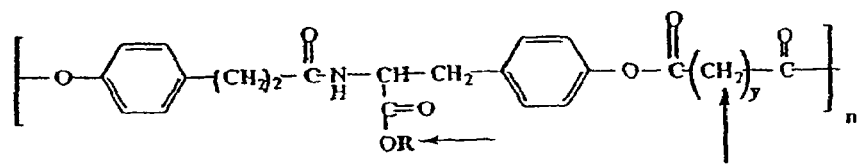
FIG. 1
desaminoCys-homoArg-Gly-Asp-Trp-Pro-Cysamide
SEQ ID NO: 1
FIG. 2
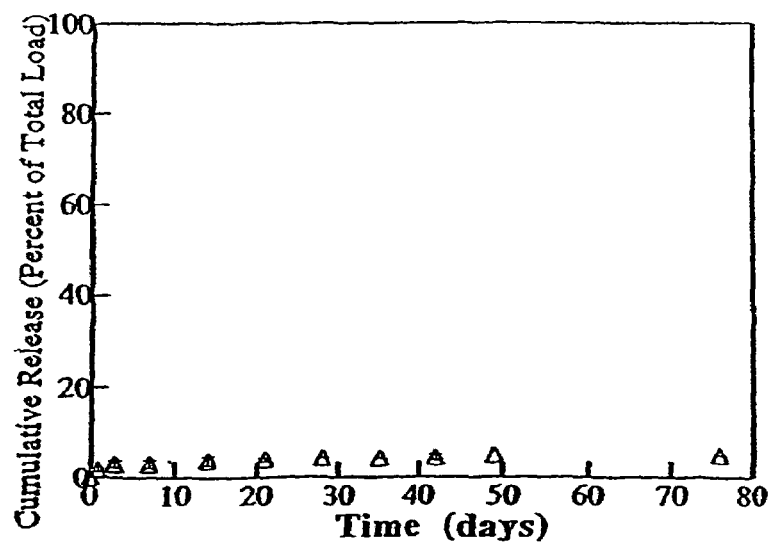
FIG. 3

SEQUENCE LISTING

```
<160> NUMBER OF SEQ ID NOS: 1

<210> SEQ ID NO 1
<211> LENGTH: 7
<212> TYPE: PRT
<213> ORGANISM: Homo sapiens
<220> FEATURE:
<221> NAME/KEY: MOD_RES
<222> LOCATION: (1)..(1)
<223> OTHER INFORMATION: desaminoCys
<220> FEATURE:
<221> NAME/KEY: MOD_RES
<222> LOCATION: (2)..(2)
<223> OTHER INFORMATION: homoArg
<220> FEATURE:
<221> NAME/KEY: MOD_RES
<222> LOCATION: (7)..(7)
<223> OTHER INFORMATION: Cysamide

<400> SEQUENCE: 1

Cys Arg Gly Asp Trp Pro Cys
1               5
```

PHARMACEUTICAL FORMULATION FOR REGULATING THE TIMED RELEASE OF BIOLOGICALLY ACTIVE COMPOUNDS BASED ON A POLYMER MATRIX

CROSS-REFERENCE TO RELATED APPLICATION

The present application claims priority benefit under 35 U.S.C. §371 of International Application No. PCT/US01/00030 filed Jan. 2, 2001, which, in turn, claims priority benefit under 35 U.S.C. §119(e) of U.S. Provisional Application No. 60/174,137 filed Dec. 31, 1999.

BACKGROUND OF THE INVENTION

The present invention relates to a new approach to the delayed or pulsed release of biologically active compounds having pharmaceutical activity, particularly peptides such as INTEGRILIN™, from a polymer matrix. In this system no complicated barrier mechanism is required to prevent the release of the peptide during the lag time, a high loading of the water-soluble peptide is readily achieved, and the length of the delay of the release of the peptide is easily controlled.

Previously, limited release of INTEGRILIN™ was reported from poly(DTH adipate), a member of the tyrosine-derived polyarylates, despite high loadings of the peptide (30% w/w). Subsequent investigations indicated that interactions between the peptide and the polymer were responsible for the minimal release (~5% of the loaded peptide). Since hydrogen bonding was a component of the interactions, the release of the peptide from poly(DTH adipate) was demonstrated to be sensitive to the pH within the polymer matrix.

The literature is replete with examples of the delayed or pulsed release of active agents using polymeric materials. However, it is possible to divide these systems into two basic categories; those that depend on an environmental stimulus to induce release of the active agent from the polymeric matrix and those that are designed to release the drug after particular intervals of time have elapsed. Examples of environmental stimuli that have been used for this application are electrical impulses, pH or temperature changes, application of magnetic fields, or ultrasound.

Those systems that are time-controlled can further be divided into those that use a barrier technology that is placed around the active agent that is designed to degrade or dissolve after a certain time interval, and those that use the degradation of the polymer itself to induce the release of the active agent.

One approach of this category has been to prepare a polymeric hydrogel composed of derivitized dextran and to incorporate into the hydrogel, a model protein, $I_gG$, with an enzyme, endo-dextranase, that degrades the hydrogel. It was observed that without the enzyme the release of the protein was very slow. However, when the enzyme was included in the formulation, the release rate was dependent on the concentration of the enzyme. At high concentrations, the release was fast and complete. At low concentrations, the release was delayed.

A correlation was found between the delay time and the rate of degradation of the hydrogel. The interpretation of the data was that the mesh size of the hydrogel was too small for efficient diffusion of a large protein molecule such as $I_gG$, but as the enzyme degraded the polymer, the mesh size increased and diffusion was unimpeded.

Delayed release in association with hydrolytic degradation of the polymer has also been investigated. Heller's poly(ortho esters) are viscous ointments at room temperature and when mixed with a model protein, lysozyme, demonstrated a delayed release profile. The length of the delay time was found to correlate with polymer molecular weight and alkyl substituent of the polymer. These experiments, however, are limited by the fact that all of the drug release experiments were conducted at room temperature, perhaps, because the polymers are viscous at room temperature, but not at the physiological temperature of 37° C.

Ivermectin, a water insoluble antiparasitic agent for veterinary applications, was encapsulated in PLGA (50:50) microspheres and the subsequent pulsed release of this agent, in vivo, was shown to be dependant on the degradation rate of the polymer matrix. Pulsed and delayed release of active agents from PLGA microspheres was most intensely studied by Cleland et al. The PLA or PLGA microspheres are processed using a high kinematic viscosity of polymer solution and a high ratio of polymer to aqueous solution. This produces dense microspheres, which require severe bulk erosion to release the drug. These conditions yield microspheres that have low loading (generally 1% w/w), moderate bursts, and lag times during which significant leaching of drug occurs.

SUMMARY OF THE INVENTION

The technology described in this disclosure represents a departure from the prior art. In this system, bonding interactions between a polymer and an active compound are used to inhibit the release of the active compound, and the polymeric degradation products are used to control the length of time preceding release of the active compound. The bonding interactions are composed of hydrogen bonding and hydrophobic forces and develop when a highly functional polymer is employed.

Therefore, according to one aspect of the present invention, a formulation containing a biologically active compound is provided, having a structure with hydrogen bonding sites, blended with a polymer having a structure with complementary hydrogen bonding sites, the polymer forming hydrolytic degradation products that promote the release of the biologically active compound from the polymer.

The formulation thus consists of two components, a polymer and an active compound blended together. The present invention thus provides a formulation system that uses the degradation products of selected polymers to trigger the release of the active compound from the matrix of the polymer. Using this method, active compounds can be very simply formulated with the polymer and be programmed to be released at desired intervals, requiring no sophisticated barriers to prevent the premature release of the active agent.

There are many drugs that are more effective when given to the patient in a pulsatile manner as opposed to a continuous release fashion. For example, an area of great interest, currently, for this type of delivery system is single-shot immunity. Immunity is best induced by a pulsatile delivery of the agent, hence the need for booster shots. It has been suggested that it would be more economical and effective, especially in third world countries, if a tetanus toxoid or gp120 (under development for an AIDS vaccine) could be implanted once into the patient and the boosters be automatic and preprogrammed from the implanted or injected device.

Therefore the present invention also includes a method for the pulsatile delivery of a biologically active compound to a patent in need thereof comprising administering to the patient the formulation of the present invention.

This type of drug delivery is not only important for amino acid drugs but also for hormonal based drug delivery. Fertility and birth control drug therapy for both animals and humans is not continuous, but rather cyclic in nature since these therapies work synergistically with the menstrual cycle and the corresponding hormonal flux. This is another direction in drug delivery in which this type of delayed pulsed release of an active agent would be applicable.

Agricultural applications which require the timed dosing of fertilizers, weed-killers, and other active agents is another area where this invention would be important.

BRIEF DESCRIPTION OF THE DRAWINGS

FIG. 1 depicts the chemical structure of tyrosine-derived polyarylates;

FIG. 2 depicts the amino acid sequence of INTEGRILIN™ of SEQ ID NO 1;

FIG. 3 depicts release from poly(DTH adipate) films containing 30% (w/w) peptide;

DETAILED DESCRIPTION OF THE PREFERRED EMBODIMENTS

Figure 4:
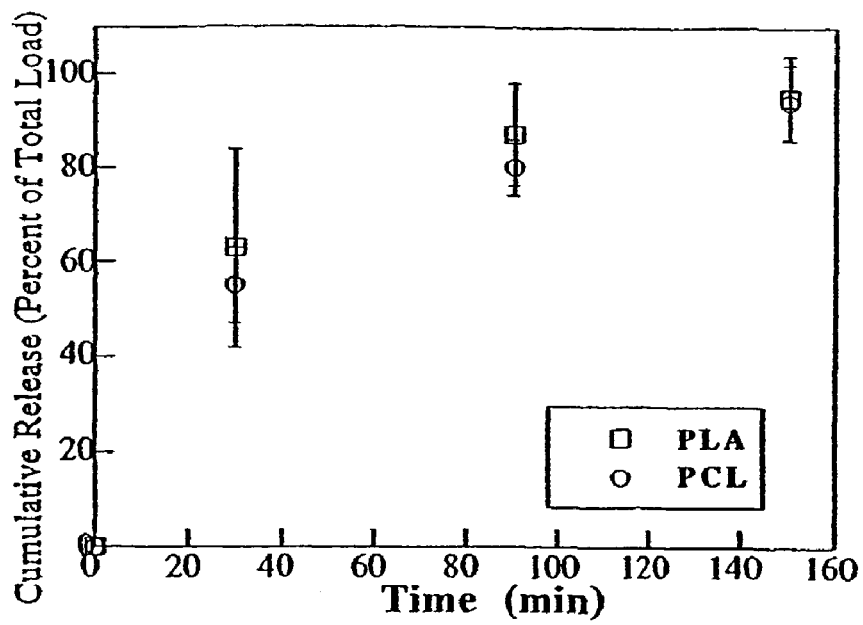
FIG. 4 depicts release from D,L -PLA and poly(ε-caprolactone) films containing 30% (w/w) peptide.

In its broadest embodiment, polymers that are suitable for use in the present invention are any polymer that contains hydrogen-bonding sites as part of its structure and degrades to form products that promote the release of a biologically active compound from the polymer. Biocompatible polymers are required for biomaterial end-use applications.

Preferred polymers are copolymers containing a hydrophilic monomer and a hydrophobic monomer. In a more preferred embodiment, the copolymer is selected from the tyrosine-derived polyarylate libraries disclosed in WO 99/24107 and WO 99/52962, the disclosures of both of which are incorporated herein by reference. The copolymers of WO 99/24107 contain a hydrophilic monomer with a pendant carboxylic acid group, desaminotyrosyltyrosine, which degrades to form acidic degradation products. The other monomer, a desaminotyrosyltyrosine ester, also contains hydrogen bonding sites for retention of the active compound. A water soluble yet hydrophobic dicarboxylate monomer forms polyarylate linkages between the two diols.

Members of the tyrosine-derived polyarylate library all share the same highly functional structural template but are distinguished from one another by subtle structural changes. The functional groups of the main template provide sites for interactions. These are pi stacking of its aromatic rings with an aromatic ring of a peptide, or hydrogen bonding of the α-amido carboxylate region with a corresponding group in the peptide. The small structural variations between members allow the fine-tuning of these interactions to suit particular proteins or peptides.

Also preferred are any of the copolymers that can be derived from the tyrosine-derived diphenol compounds of U.S. Pat. No. 5,587,507 and the tyrosine-derived dihydroxy monomers of WO 98/36013, the disclosures of both of which are also incorporated herein by reference, using the process of WO 99/24107 for forming free carboxylic acid moieties. In addition to the above-referenced polyarylates, examples include the polycarbonates of U.S. Pat. No. 5,099,060, the polyiminocarbonates of U.S. Pat. No. 4,980,449, the polyphosphazenes and polyphosphates of U.S. Pat. No. 5,912,225, polyurethanes, including the polyurethanes of U.S. Pat. No. 5,242,997, the random poly(alkylene oxide) block copolymers of U.S. Pat. No. 5,658,995, and a wide range of other polymers that can be derived from the above-referenced tyrosine-derived diphenol compounds, the tyrosine-derived dihydroxy compounds and similar peptides. All of the above referenced patent publications are incorporated herein by reference. Notably, corresponding polymers of the tyrosine-derived dihydroxy compounds can be made by any of the processes of any of the above-referenced patents disclosing polymers of tyrosine-derived diphenol compounds.

A particularly preferred copolymer is the desaminotyrosyltyrosine (DT) copolymer of poly(desaminotyrosyltyrosine hexyl ester adipate) (Poly(DTH adipate)), depicted in FIG. 1 (y=4; R=hexyl). Poly(DT-CO-DTH adipates) having a weight-average molecular weight between about 80,000 and about 200,000 daltons is particularly preferred.

In a preferred embodiment, the present invention uses pH sensitivity to control the release of an active compound. It was discovered that the accumulation of acidic polymer degradation residues in the matrix of a polymer/peptide blend weakened the interactions between the peptide and the polymer so that the peptide could be released. An inverse correlation was demonstrated between the mole percent of acid moieties in a polymer and the length of the lag time preceding release indicating that timed release of a peptide, or any active agent with hydrogen bonding sites, can be controlled by mole percent of acid moieties in a polymer.

Any biologically active compound with hydrogen-bonding sites that can be physically dispersed within the polymer can be used as an active compound for release. Examples of hydrogen bonding sites include primary and secondary amines, hydroxyl groups, carboxylic acid and carboxylate groups, carbonyl (carboxyl) groups, and the like. While one can apply the current invention to any active compound that has hydrogen bonding sites, including natural and unnatural antibiotics, cytotoxic agents and oligonucleotides, amino acid derived drugs such as peptides and proteins seem to be most appropriate for this technology. The compositions of the present invention overcome some of the difficulties encountered in previous attempts to formulate controlled release devices that show reproducible release profiles without burst and/or lag effects. In its most preferred embodiment, the active compound is a peptide that is stable under mildly acidic conditions.

Peptide drugs suitable for formulation with the compositions of the present invention include natural and unnatural peptides, oligopeptides, cyclic peptides, library generated oligopeptides, polypeptides and proteins, as well as peptide mimetics and partly-peptides. Peptide drugs of particular interest include platelet aggregation inhibiting (PAI) peptides, which are antagonists of the cell surface glycoprotein IIb/IIIa, thus preventing platelet aggregation, and ultimately clot formation. Preferred PAI peptides include the PAI peptides disclosed by WO 90/15620, the disclosure of which is incorporated herein by reference, particularly INTEGRILIN™ (FIG. 2), a medically useful cyclic PAI heptapeptide.

The compositions of the present invention are suitable for applications where localized drug delivery is desired, as well as in situations where systemic delivery is desired. Therapeutically effective dosages may be determined by either in vivo or in vitro methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate of the drug from the formulations of this invention are also varied within the routine skill in the art to determine an advantageous profile, depending on the therapeutic conditions to be treated.

A typical dosage might range from about 0.001 mg/kg to about 1000 mg/kg, preferably from about 0.01 mg/kg to about 100 mg/kg, and more preferably from about 0.10 mg/kg to about 20 mg/kg. Advantageously, the compounds of this invention may be administered several times daily, and other dosage regimens may also be useful.

The compositions may be administered subcutaneously, intramuscularly, colonically, rectally, nasally, orally or intraperitoneally, employing a variety of dosage forms such as suppositories, implanted pellets or small cylinders, aerosols, oral dosage formulations and topical formulations, such as ointments, drops and transdermal patches. Liposomal delivery systems may also be used, such as small unilamellar vesicles, large unilamellar vesicles and multilamellar vesicles.

The following non-limiting examples set forth herein below illustrate certain aspects of the invention. All parts and percentages are by weight unless otherwise noted and all temperatures are in degrees Celsius. The PAI peptide was obtained from COR Therapeutics of South San Francisco, Calif., and used without further purification. Solvents were of "HPLC grade" and were obtained from Fisher Scientific of Pittsburgh, Pa.

EXAMPLES

INTEGRILIN™ (antithrombotic injection) was chosen as the model peptide to explore the drug delivery applications of these materials (FIG. 2). This compound is a synthetic cyclic readily water-soluble heptapeptide which is a highly potent glycoprotein IIb/IIIa antagonist. This compound has successfully demonstrated antithrombogenic behavior in vivo and devices fabricated by the formulation of this peptide into a polymer matrix with this property would have many useful cardiovascular applications. In addition, this polymer contains an RGD sequence and therefore a device containing this peptide could possibly find applications as a component in scaffolds for tissue regeneration.

The blend of INTEGRILIN™ and poly(DTH adipate) was described in U.S. Pat. No. 5,877,224, the disclosure of which is incorporated herein by reference. There, it was mentioned that formulating films from these components using the coprecipitation melt-press technique resulted in specimens that released only trace amounts of peptide when incubated in PBS at 37° C. This was unexpected because the peptide is readily water-soluble.

Polymer Synthesis and Specifications

Tyrosine derived polyarylates were synthesized as described in U.S. Pat. No. 5,877,224 and in WO 99/24107. Poly(DTH adipate) R=hexyl and y=4), was the polymer specifically chosen for this study though many of the physical phenomena reported here for this polymer have been observed with others in this polymer family. The polymers used had molecular weights ranging between 80-120 kDa. The particular polymers synthesized were poly($DT_{0.05}$-co-$DTH_{0.95}$ adipate, Poly($DT_{0.10}$-co-$DTH_{0.90}$ adipate), and poly($DT_{0.15}$-co-$DTH_{0.85}$ adipate). The molecular weights of the polymers used ranged from 60-80 kDa. D,L -PLA and poly($\epsilon$-caprolactone) were purchased from Medisorb and Aldrich, respectively. Both were of molecular weight 100 kDa and fabricated into release devices in the same manner as the poly(DTH adipate).

Fabrication of Release Devices

The peptide was obtained from COR Therapeutics, Inc. The peptide, as received, was 98-99% pure and used without further purification. Compression molded films were fabricated from a co-precipitate containing 30% peptide and 70% polymer by weight. This co-precipitate was prepared by dissolving 0.15 g of peptide in 5 ml of methanol (HPLC grade) and 0.35 g polymer in 5 ml of methylene chloride (HPLC grade) and mixing the two solutions together to form a clear solution. This resultant solution was added drop-wise into 100 ml of stirred ethyl ether maintained at −78° C. White spongy precipitates were formed, filtered using a sintered glass filter, and dried under vacuum. After drying the co-precipitate was compression molded at 90° C. under a pressure of 5,000 psi. Films with a thickness of 0.1 mm (±0.02 mm) were obtained.

Device Characterization

Peptide loading was determined by dissolving 10.0 mg of a film in THF (HPLC grade) (1.0 ml) in a 10 ml volumetric flask and adding PBS (phosphate buffer saline) until the 10 ml line. The mixture was stirred for a minimum of 6 hours followed by HPLC analysis of the drug content in the aqueous medium. Methylene chloride replaced THF when characterizing samples composed of PLA or poly(ε-caprolactone) due to their insolubility in THF.

Peptide Release Study

Films were cut into 0.5 cm$^2$ squares. The mean mass of the samples was 21 mg (±5). Each specimen was individually placed into 20 ml glass scintillation vials containing 10 ml of phosphate buffered saline (pH 7.4, 37° C.). The standard PBS solution used was composed of 10 mM phosphate buffer saline, 138 mM NaCl and 2.7 mM KCl. The buffer was changed at each time point and analyzed by HPLC for release of the peptide. There was a minimum of three samples per time point, each sample originating from a different film. The HPLC method involved a 3 cm C-18 Perkin Elmer cartridge column with a gradient mobile phase which began at 80% water/20% acetonitrile and ended with 75% water during a period of 5 minutes at a flow rate of 1 ml/min. Both the acetonitrile and water contained 0.1% (v/v) trifluoroacetic acid. The column was calibrated with known concentrations of the peptide dissolved in PBS to establish a calibration curve and the INTEGRILIN™ contained in the buffer of each sample was quantified using this curve. The HPLC pump used was a Perkin Elmer Series 410 LC pump and the detector used was a PE LC-235 diode array UV-VIS detector set at 280 nm. The data collected was analyzed using a PE Nelson 3000 Series Chromatography Data System.

At designated times, the samples were removed, rinsed with deionized water, blotted with a Kimwipe tissue and either placed in a vial for subsequent vacuum drying for mass retention and molecular weight retention studies or used for thermal gravimetric analysis (TGA) water uptake studies. Those devices that were not needed for gel permeation chromatography (GPC) or TGA studies were dissolved in organic solvent subsequent to drying and the peptide content extracted to ensure that all loaded peptide was accounted for.

Molecular Weight Determination of the Polymers Using GPC

The molecular weights of the poly(DTH adipate) samples were calculated relative to a set of monodispersed polystyrene standards (Polymer Laboratories, Ltd. Church Station, U.K.) without further corrections. The GPC chromatographic system consisted of a Waters 510 HPLC pump, a Waters 410 differential refractometer detector, and a Digital Venturi's 466 PC running Millenium (Waters Corp.) software for data processing. Two PL-gel columns 30 cm in length (pore sizes of 10$^3$ and 10$^5$ Å; Polymer Laboratories Ltd.) operated in series at a flow rate of 1 ml/min in THF.

Samples composed of PLA or PCL were dissolved in methylene chloride instead of THF, but otherwise analyzed in the same way as the poly(DTH adipate) samples.

Water Content Determination Using Thermogravimetric Analysis (TGA)

A small sample (10 mg) was cut from a specimen and placed in an aluminum TGA pan. The sample was heated under a nitrogen flow at a rate of 10° C./min from room temperature to 225° C. The water uptake was measured by the loss in weight of the sample as it was heated from room temperature until 150° C.

Water Content Determination Using the Microbalance

At pre-determined time points, the samples were removed from the buffer, rinsed with deionized water and blotted dry. The sample's wet weight ($W_w$) was immediately taken using an electronic balance. The dry weight ($W_d$) was taken after the sample was dried under vacuum for at least two weeks, by this time constant weight was achieved. The amount of water uptake was calculated from the following equation:

$$\% \text{ Water uptake} = [(W_w - W_d)/W_d] \times 100 \quad \text{Eq. (2.1)}$$

Differential Scanning Calorimetry Analysis (DSC) to Measure the Melting Point of the Peptide and Melt Transitions in the Polymer Film DSC was used to determine the melting point of the peptide. A sample of approximately 2 mg of peptide was weighed out and sealed in a crimped aluminum DSC pan. The sample was heated at 12° C./min from room temperature to 200° C., under nitrogen flow. DSC was also used to determine whether there is a melting transition associated with the polymer films that contain 30% (w/w) peptide. A sample size of 6 mg of film was sealed in a crimped aluminum DSC pan and heated at 12° C./min until 200° C., under nitrogen flow. Melting point of the sample was determined by the temperature at which the sharp endotherm of melting occurred. AR data was analyzed using the first-run thermogram. An empty aluminum pan was used as a reference in each experiment. The instrument used was a DSC 910 (TA instruments). The instrument was calibrated with indium (m.p.=156.61° C.) before use.

Percent Mass Retention Study

The percent mass retention of the samples was calculated in the following manner. The sample was removed from the PBS incubation medium, rinsed in deionized water, and blotted with a Kimwipe tissue. It was placed in a fresh vial and dried under vacuum for 2 weeks. Following this dessication period, it was weighed ($W_d$). The mass obtained following incubation and drying was compared to the initial mass ($W_o$). The formula for calculating percent mass retention is the following:

$$\% \text{ Mass loss} = [(W_o - W_d)/W_o] \times 100 \quad \text{Eq. (2.2)}$$

Fabrication and Incubation of Films Under Acidic Conditions

The same formulation protocol mentioned above was followed for these films, with the exception that concentrated HCl (12 molar) was added drop-wise to the stirred peptide/methanol solution until the pH, as measured by a pH meter dropped from 6.8 to 2.

The acidic media for the in vitro incubation studies conducted at pH of 2 was prepared in the following manner. Standard PBS solution was used and 12 M HCl was added drop-wise into the PBS until the PBS until the pH meter indicated that the desired pH had been obtained.

Incubation of Films Under Varying Ionic Strength Conditions

Three sets of films were prepared in the standard method mentioned above, one set was incubated in HPLC water, used as is. Another was incubated in standard PBS buffer. The last set was incubated in PBS buffer that was twice the concentration of the standard PBS solution.

The Effect of the Peptide on the Glass Transition Temperature of Poly(DTH Adipate)

The glass transition temperature of sets of films was measured using Dynamic Mechanical Analysis (DMA). Measurements were performed on a DMA 983 from TA Instruments in a flexural bending deformation mode of strain. Each set of films contained a different weight percentage of peptide ranging from 0%-30% (w/w) of peptide. Samples of approximate size 5×10×1 mm were cut from the films and mounted on the instrument using low mass clamps, after calibrating the instrument with the low mass clamps. The samples were cooled using a liquid nitrogen cooling accessory to −30° C. and heated at a rate of 4° C./min until 70° C. The frequency was fixed at 1 Hz and the amplitude was 1 mm. The glass transition was read from the maxima of the E" peak.

Reduction of the Peptide Using Dithiothreitol (DTT)

INTEGRILIN™ (4.12 mg) was placed in a 25 ml round-bottom flask. To this flask was added 50.12 mg of dithiothreitol. A minimun of 20 moles of DTT was required per disulfide bridge (this is 62 moles of DTT per disulfide bridge). Then 3 ml of water was added and flask was stoppered. The contents of flask were stirred with a magnetic stirrer. Every few hours, an aliquot of reaction mixture was removed from the flask, diluted with HPLC water, and analyzed with HPLC. As the reaction continued, the peak at 1.7 minutes corresponding to the intact peptide decreased and the peak at 2.5 minutes corresponding to the peptide with the cleaved disulfide bridge increased. Virtually all of the peptide had been reduced after stirring overnight.

Following the conversion, the reaction mixture was lyophilized overnight. In order to extract the reduced product, 5 ml of diethyl ether was added to dissolve the DTT and precipitate the peptide. This mixture was stirred for 3 hours and the resulting suspension was filtered using filter paper. The filtered material was dried under vacuum overnight.

The presence of free SH groups was assayed in the following manner. A saturated solution of lead acetate in ethanol was made and a few milliliters of this solution were poured into the vial containing the dried reduced peptide. A yellow color developed indicating the presence of the lead sulfur complex. As a control, equal volume of this lead solution was added to the peptide with the intact disulfide bridge and no yellow color was detected.

Evidence for and Investigation of Interactions between the Peptide and Poly(DTH Adipate)

Formulation of INTEGRILIN™ with Poly(DTH Adipate)

Films composed of poly(DTH adipate) containing loadings of 5, 10, 15, 20, and 30% (w/w) peptide were prepared. Films containing even, the highest loading were clear and flexible. In contrast, the films composed either of $D,L$-PLA or poly(ε-caprolactone) (PCL) containing the same load of peptide were opaque and brittle. The clarity of the peptide/polyarylate films indicated that the phase separation in the case of the peptide and poly(DTH adipate) was sufficiently reduced that the separate polymer and peptide domains were too small to scatter light. This suggested an enhanced compatibility of peptide and tyrosine-derived polymer relative to the $D,L$-PLA or PCL and peptide.

The flexibility of the polyarylate films that contained peptide relative to those composed of the peptide and either of aliphatic polyesters can be explained by the lower glass transition temperature of the polyarylate (37° C.) as compared to that of PLA (52° C.), and the amorphous nature of the polyarylate as compared to PCL.

Release of Peptide from Films Incubated at 37° C. and at pH=7.4

In this experiment the in vitro release behavior of the peptide, under simulated physiological conditions, from various polymer matrices Was observed. Both the aliphatic polymers released the peptide completely within three hours. In contrast, the poly(DTH adipate) demonstrated only trace release, over a period of 77 days, under the identical conditions (FIGS. 3 & 4).

Percent Mass Retention of Incubated Samples

Figure 5:
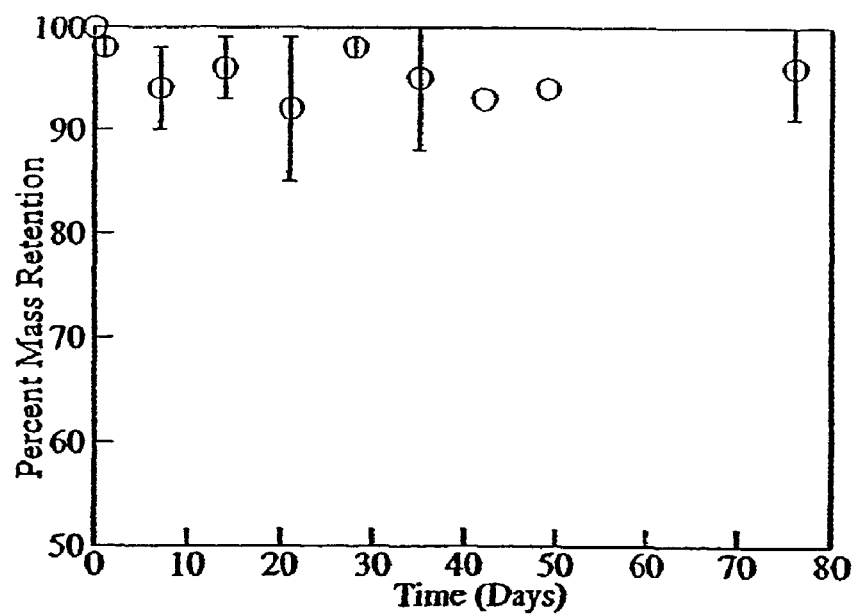
FIG. 5 depicts percent mass retention of poly(DTH adipate) samples containing 30% (w/w) peptide.
Figure 6:
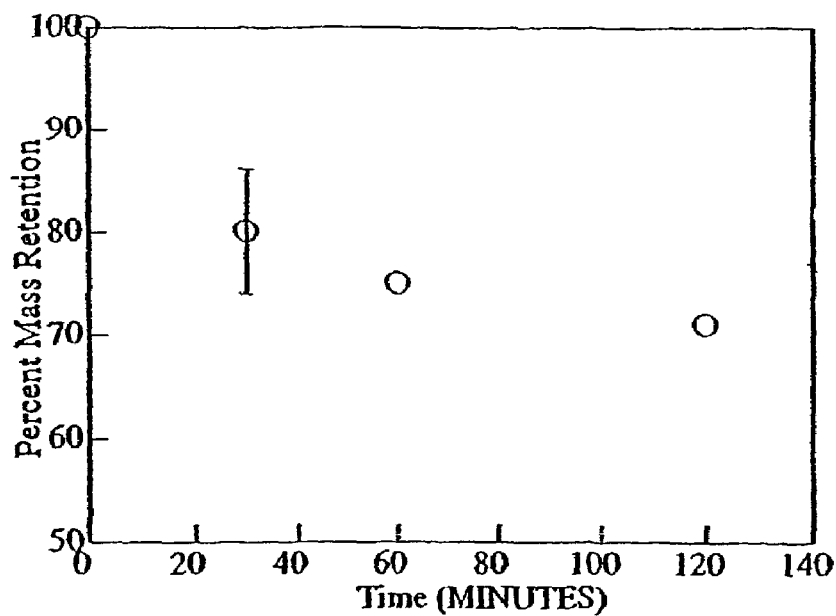
FIG. 6 depicts percent mass retention data for D,L -PLA samples containing 30% (w/w) peptide.

Poly(DTH adipate) samples containing 30% (w/w) peptide lost on average 5% mass during the 77 day incubation period (FIG. 5). In contrast, the $D,L$-PLA samples that were formulated in the identical fashion as the poly(DTH adipate) samples lost about 30% of their mass within two hours (FIG. 6). The results of these experiments, therefore, were consistent with the data obtained from the HPLC. In the case of the poly(DTH adipate) films containing 30% (w/w) peptide, the HPLC data indicate that these films released less than 10% of the loaded peptide (FIG. 3). This translates into a mass loss for the entire sample of about 3% over the 77 day period. This is in agreement with the average 5% mass loss observed for these samples.

In contrast to the poly(DTH adipate) samples that demonstrated minimal mass loss, the PLA samples showed extensive mass loss. These film samples also contained 30% (w/w) peptide. HPLC data indicated that these samples released all of the peptide that they contained, this translates into a 30% mass loss over the three hour incubation period. The resulting percent mass retention data is about 70% for these samples is therefore in agreement with the HPLC results. Furthermore, since the peptide was released so rapidly by the PLA and PCL matrices, it can be concluded that the peptide is small enough to readily diffuse through the polymer chains and the development of pore structures and interconnecting channels is not necessary to release the molecules of peptide that are deep within the film. Therefore there should be minimal impedance for release of the peptide from the polyarylate.

Measurement of Water Absorption by Polymer Films During Incubation

Figure 7:
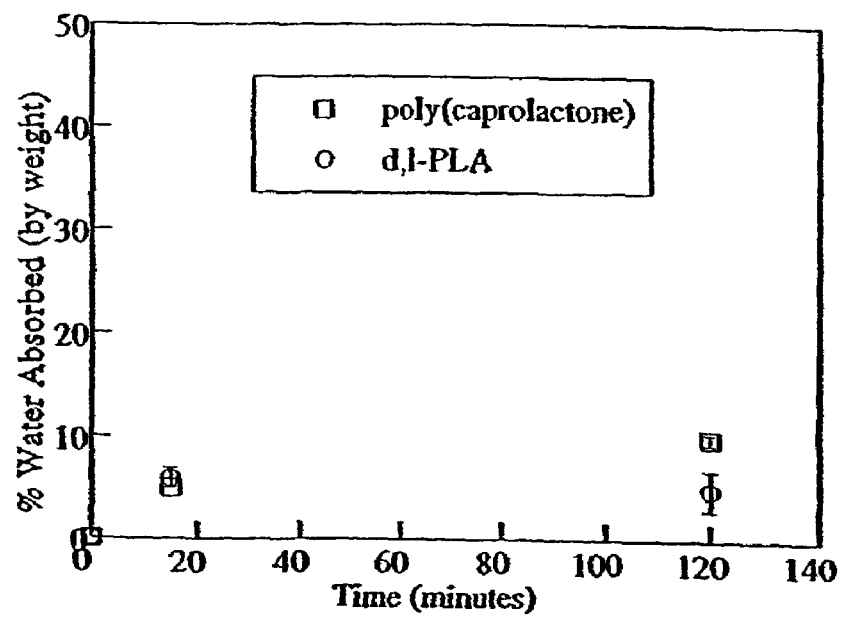
FIG. 7 depicts percent water absorption by films of PCL and PLA containing 30% (w/w) peptide.
Figure 8:
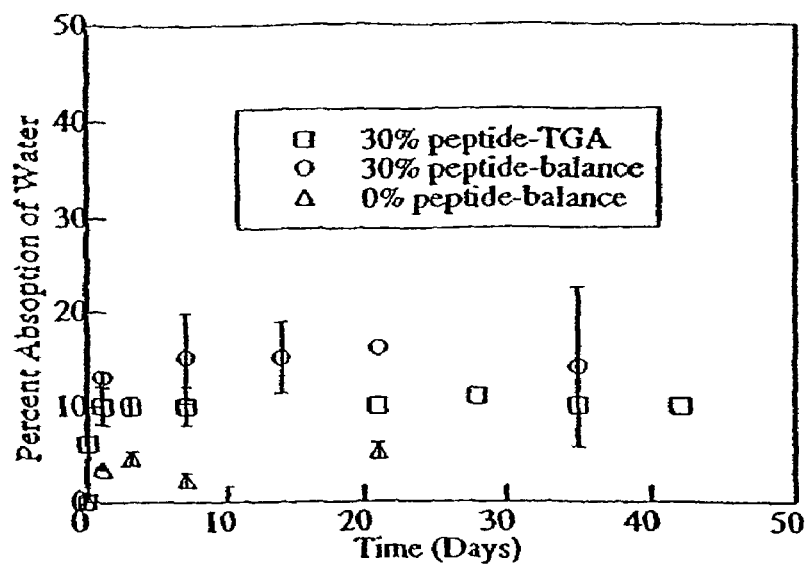
FIG. 8 depicts percent water absorption by films of poly (DTH adipate) both with and without peptide.

Specimens of poly(DTH adipate) containing 30% (w/w) peptide absorbed about 10% by weight water within the first day and maintained that level of swelling throughout the entire incubation period. Also the presence of the peptide increases the water absorption of the polymer from about 3% by weight to 10% by weight (FIG. 8). Samples of PLA and PCL containing identical loading of peptide to the poly(DTH adipate) also absorbed water within that range during the 2-3 hours that they were incubated (FIG. 7).

The Effect of the Peptide on the Molecular Weight of the Polymer

Figure 9:
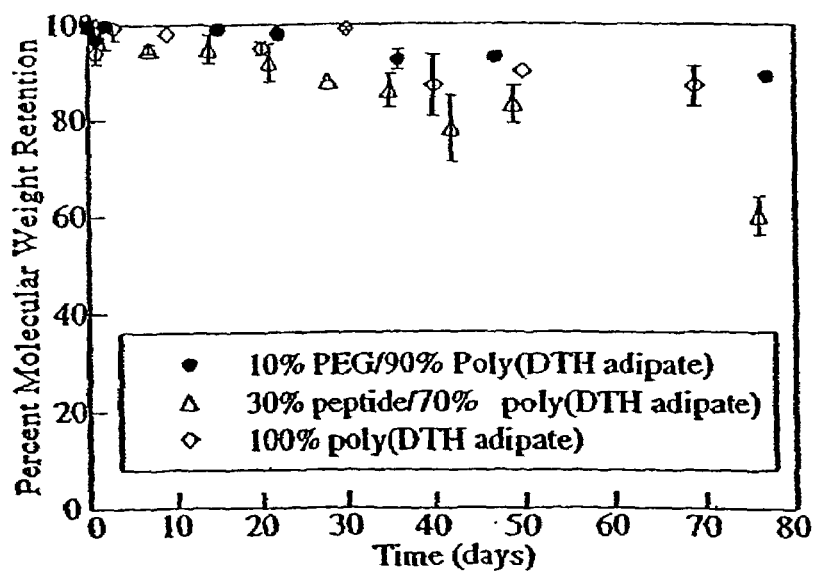
FIG. 9 depicts percent molecular weight retention of neat poly(DTH adipate) samples to that of poly(DTH adipate) containing 30% (w/w) peptide, and to that of 10% PEG/90% poly(DTH adipate)

One of the amino acid residues on the peptide is an aspartic acid. Aspartic acid is a moiety that introduces acidity into the polymer when the polymer is blended with the peptide. Consequently, an investigation of the molecular weight degradation of the polymer was made and compared to rate of degradation for the neat poly(DTH adipate) (FIG. 9).

As an additional control, samples composed of a blend of 10% (w/w) PEG and 90% (w/w) poly(DTH adipate) were included in these studies because these samples absorb 20% by weight water as measured by the TGA. This represents more water than is absorbed by the polymer samples containing 30% (w/w) peptide and functions as a control for the effect of the added water on the molecular weight degradation of the polymer. The results of these studies were that the samples containing peptide did degrade at a faster rate than the samples that did not contain peptide. After a period of over 2 months the poly(DTH adipate) samples containing 30% (w/w) peptide had undergone 40% molecular weight degradation. In contrast, those samples without peptide demonstrated almost no degradation during this time period.

In addition, the increased amount of water in the polymer matrix did not affect the rate of molecular degradation at all. There did not appear to be any significant difference in the rate of molecular weight degradation between the poly(DTH adipate) samples containing PEG and the neat samples. It was the presence of the peptide that had the catalytic effect on the degradation of the polymer. However, this increase in degradation rate was not significant enough to affect the release of the peptide.

The glass transition temperature of neat poly(DTH adipate) was compared to those of poly(DTH adipate) containing 15, 20, or 30% (w/w) peptide. The results indicated that the peptide did not reduce the glass transition temperature of the polymer. In fact, in every case where peptide was present the glass transition temperature was higher relative to the neat polymer samples. The fact that there is an effect on the glass transition temperature indicates that there is a mixing on the molecular scale between the peptide and the polymer. The increase in $T_g$ with the addition of the peptide confirms that there is hydrogen bonding between the peptide and the polymer.

Effect of Ionic Strength of the Medium on the Release of the Peptide

Figure 10:
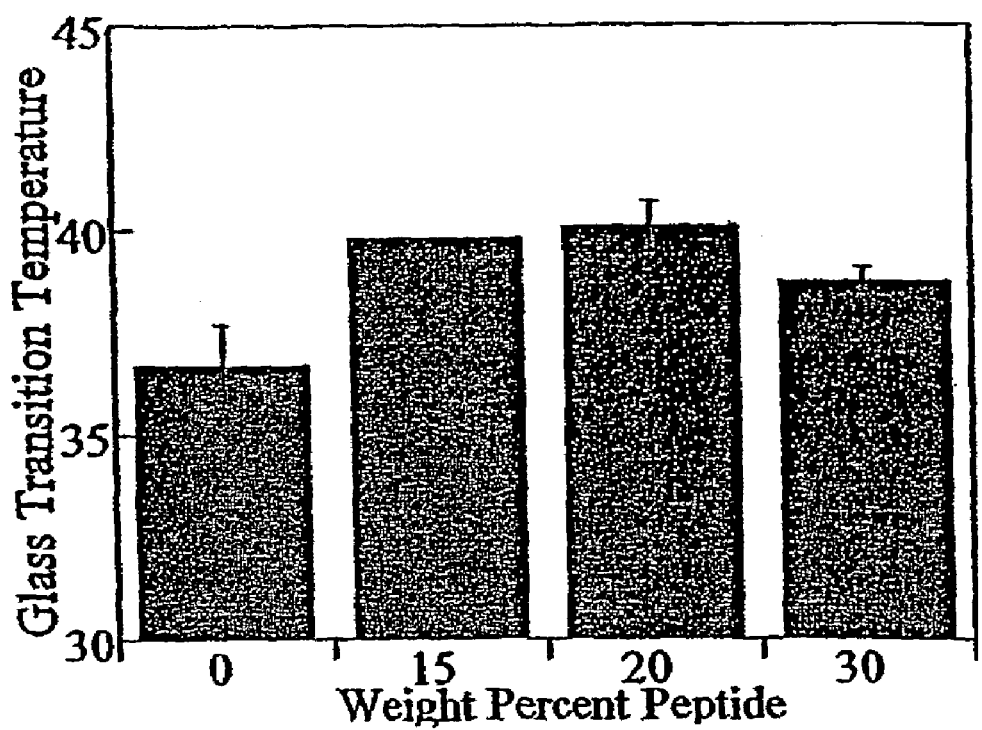
FIG. 10 depicts the effect of ionic strength on the release of 30% (w/w) INTEGRILIN™ from poly(DTH adipate) films.

Poly(DTH adipate) films containing 30% (w/w) peptide were prepared in the standard manner. The pH of the incubation media remained about 7, but the ionic strength of the release media was varied. The in vitro release of the peptide in HPLC water, in the standard PBS solution (10 mM phosphate buffer saline, 138 mM NaCl, 2.7 mM KCl), and in PBS buffer formulated at twice the concentration (20 mM phosphate buffer saline, 276 mM NaCl, 5.4 mM KCl) was measured and compared (FIG. 10). It was observed that the rate of release of peptide was four times greater in HPLC water as compar-ed to the release rate in phosphate buffer. These results suggest some hydrophobic inter-actions between the peptide and polymer. Most likely the source of these hydrophobic forces is the pi stacking of the tryptophan ring of the peptide with the phenolic ring of the polymer.

Figure 11:
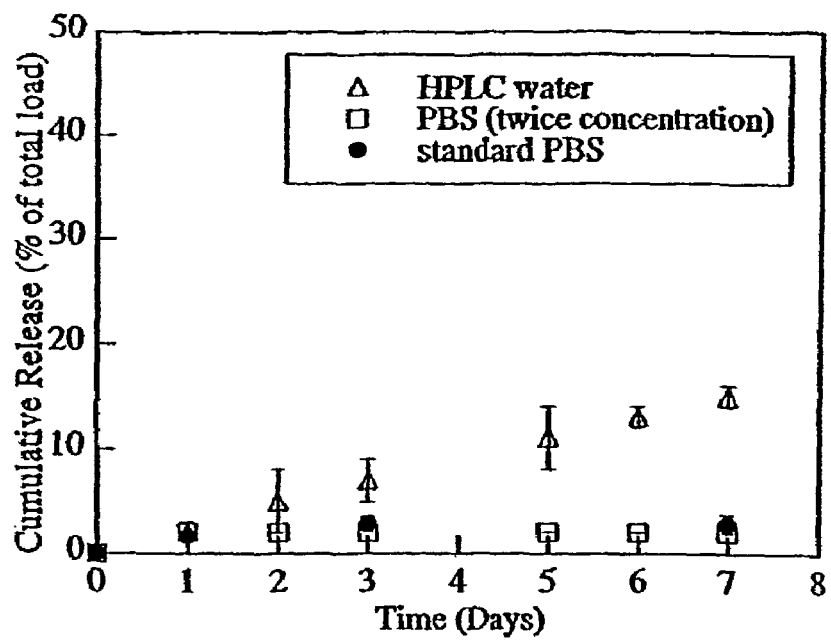
FIG. 11 depicts release from poly(DTH adipate) films containing 30% (w/w) peptide at pH 2.2 without added electrolytes.

Incubation of Poly(DTH Adipate) Films Containing 30% (w/w) Peptide in Acidic and Low Ionic Strength Conditions Samples containing 30% (w/w) peptide were prepared under standard conditions and incubated in HPLC water containing 0.1% (v/v) trifluoroacetic acid, the pH of this solution was 2.2. The release rate of the peptide, in this study, where both pH and ionic strength of the incubation media are lowered was greater (FIG. 11) than when just one factor was lowered. When just the pH was lowered, 12% of the loaded peptide was released within three days. When just the ionic strength was reduced 8% of the loaded peptide was released within three days. When both parameters were lowered simultaneously 20% of the loaded peptide was released within this time period. Despite enhanced release in these conditions, the peptide was not "dumped out" as in the case of D,L -PLA but there was a continuous diffusion of the peptide from the poly(DTH adipate) matrix.

Figure 12:
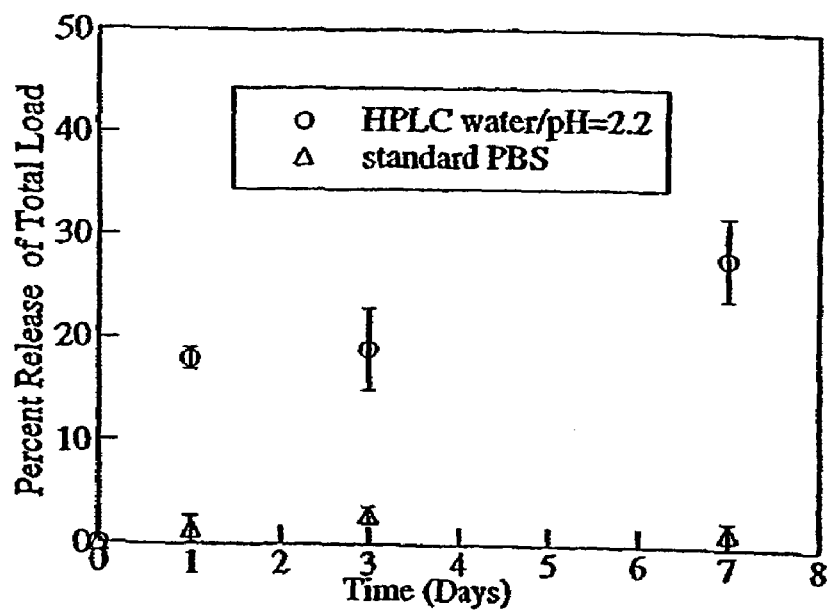
FIG. 12 depicts water uptake of poly(DTH adipate) films containing 30% (w/w) peptide at pH 2.2 without added electrolytes.

However, what was unexpected was the absorption of water under these conditions (FIG. 12). Within the first day of incubation these samples swelled three times relative to the samples incubated in the standard PBS solution, and by the seventh day these samples swelled by seven times. From FIG. 8, it can be determined that the neat polymer, by itself, does not increase its absorption of water during this initial 7 day time period when incubated in the standard PBS solution. Moreover, since this polymer is relatively hydrophobic, as determined from contact angle experiments, it would not be expected that the change in incubation conditions would promote such an increase in the percentage of water uptake by the neat polymer. Therefore, it can be inferred that it is the peptide within the matrix that is the source of this large water uptake.

Therefore, incubation in the standard PBS solution favors the interaction of the peptide with poly(DTH adipate) rather than with water, hence, there was no increase in swelling beyond the initial 10% even over many weeks of incubation in these conditions. However, in conditions where the peptide-polymer interactions are weakened, as in this case, where both the pH and ionic strength of the incubation media were lowered, there is more of a driving force for the peptide to interact with water and consequently, there was a steady increase in the swelling of the film as more peptide molecules were exposed to and interacted with water.

Under these conditions of increased acidity and lowered ionic strength the film samples also turned opaque immediately. This opaqueness, noted only under the circumstances where there was enhanced release of the peptide from the poly(DTH adipate) films, appears to be correlated with increased water absorption by the film samples. The weakening of the intensity of the peptide-polymer interactions result in an increase in water absorption and the developing opacity, is caused by the water that occupies the free volume within the polymer matrix.

The absorption of 10% by weight water was sufficient to release the peptide to completion in the case of the aliphatic polymers. However, samples whose matrix was composed of poly(DTH adipate) instead of PLA, absorbed 70% by weight water and yet not release the peptide in the same "dumping" manner that the PLA and PCL matrices did at 10% by weight of water absorption.

The interaction of the peptide with the tyrosine-derived polyarylate arises from the unique structure of the polymer in which the amide bond of each repeat unit is in close proximity to the pendent ester in the same unit. This entire region can be considered as one functional group, the α-amidocarboxylate group and can act as a pocket for the hydrogen bonding of various groups on the peptide.

Peptide-Polymer Interactions with other Tyrosine-Derived Polymers

Several other polymers were screened for the diffusion of the peptide. The loadings of peptide used in these screening experiment were lower than those used with poly(DTH adipate) but were sufficient to expect release of this readily water-soluble peptide barring any interactions to impede it.

Figure 13:
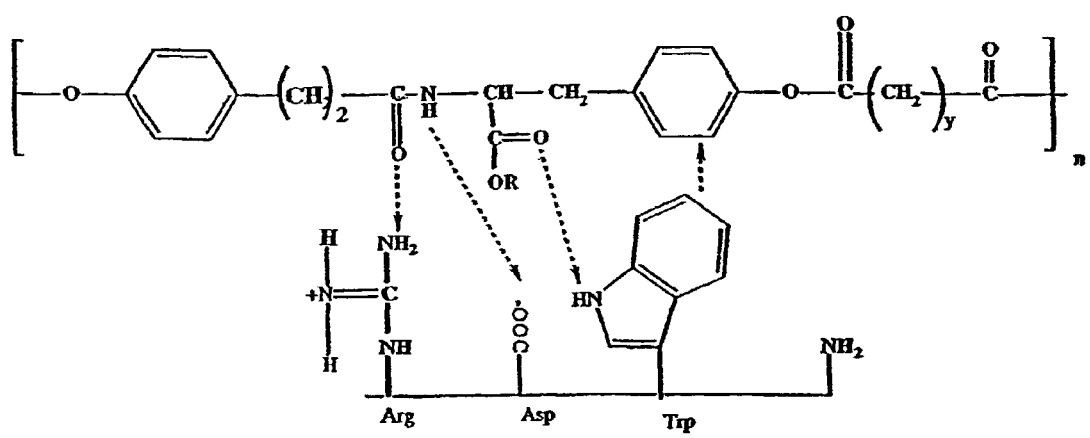
FIG. 13 depicts the chemical structure of poly(DTH dioxaoctanedioate)

Poly(DTH dioxaoctanedioate) was the first alternate but structurally related polymer that was investigated. This polymer, contains the DTH repeat unit which makes it similar to poly(DTH adipate). However, this polymer is synthesized by polymerizing DTH with dioxaoctanedioic acid (FIG. 13) instead of adipic acid. The objective of this experiment was to observe the effect of a more hydrophilic tyrosine-derived polymer on the diffusion of the peptide. It would be expected that this compound is more hydrophilic than adipic acid because there are two oxygens in the backbone spacer.

Figure 14:
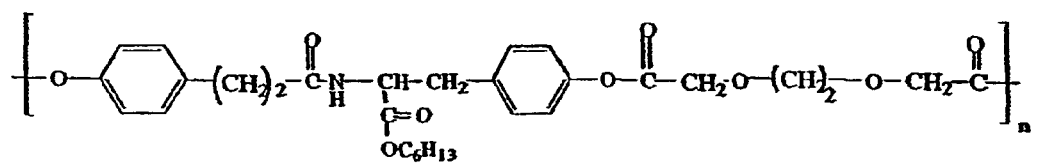
FIG. 14 depicts release of peptide from poly(DTH dioxaoctanedioate) films.

No peptide was released from these films (FIG. 14) indicating that increasing the hydrophilicity of the polymer does not have an effect on the release of the peptide. The water uptake of these films was also measured and found to be 5% by weight in the case of those films that contained 10% (w/w) peptide and 10% by weight in the case of those films containing 20% (w/w) peptide. This indicates that although the loading of the peptide is lower in these specimens there is the same amount of water in the bulk in poly(DTH adipate) specimens containing 30% (w/w) peptide as in poly(DTH dioxaoctanedioate) containing 20% (w/w) peptide. In addition, the structure of this polymer differs from poly(DTH adipate) only in the structure of the flexible backbone unit. Since the release behavior of this polymer is similar to that of poly (DTH adipate), and the structural differences between the two polymers lie only in the structure of the backbone spacer, it can be concluded that most likely it is the DTH unit that is most integral to the peptide-polymer interactions.

Figure 15:
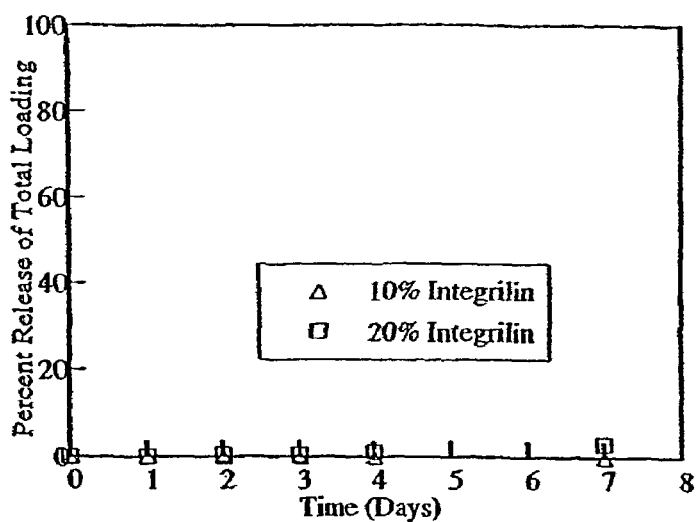
FIG. 15 depicts the chemical structure of poly(DTE carbonate)

To confirm this last conclusion, another polymer structure was substituted for poly(DTH adipate). It was the poly (DTE$_{0.95}$-co-PEG$_{(1000)0.05}$ carbonate). This polymer is a random copolymer of desaminotyrosyl tyrosine ethyl ester (DTE) and poly(ethylene glycol) (PEG) (FIG. 15). This copolymer shares the basic desaminotyrosyl tyrosine alkyl ester repeat unit with the poly(DTH adipate), but contains carbonate linkages and not ester in the backbone, and no diacid component. The absence of the diacid component and the similarity in the tyrosine-derived repeat unit should further confirm that it is the tyrosine-derived component and not the diacid that is involved in these interactions should the peptide fail to diffuse from this polymer, also. It was also postulated that since PEG is a very flexible molecule that can hydrogen bond and the length of the PEG is longer than the length of the diacid in the polyarylates, the PEG itself might interrupt the hydrogen bonds and allow release of the peptide. Films containing 10% (w/w) peptide were prepared.

Figure 16:
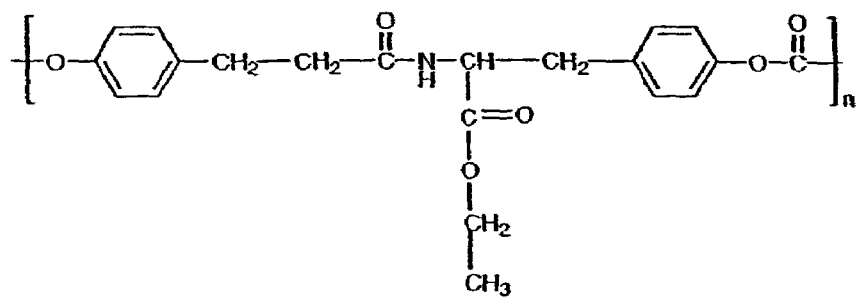
FIG. 16 depicts release of peptide from poly(DTE$_{0.95}$coPEG$_{0.05}$carbonate) containing 10% (w/w) peptide.

Peptide release from these polymers also was minimal (FIG. 16). The water uptake of these samples was also measured, during the period of incubation the film samples absorbed 10% by weight water. Again, this is the same amount of water absorbed by the PLA, PCL, and poly(DTH adipate) samples. Although the peptide loading is lower in these films it is not surprising that the water uptake is as much as samples of these other polymer systems since the PEG increases the hydrophilicity of these samples. It appears from this data and the previous data illustrating the minimal release of the peptide from polymers containing the DTR unit that the tyrosine-derived repeat unit as suggested above is the structure responsible for the absence of diffusion of the peptide from the polymer.

Figure 17:
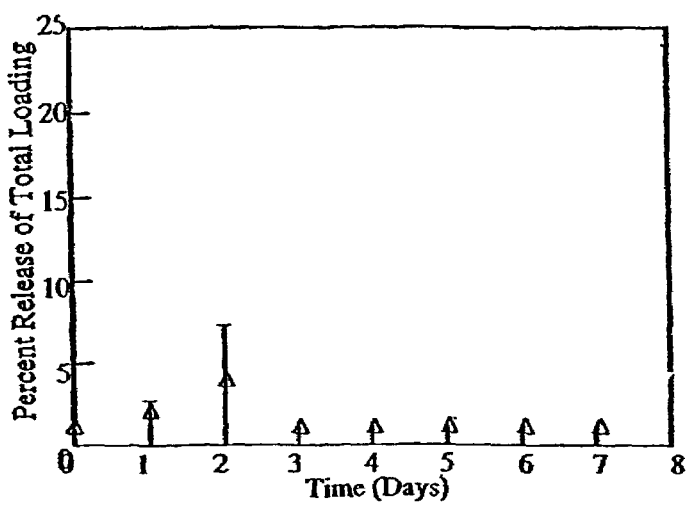
FIG. 17 depicts release of peptide from poly(DTE carbonate) samples containing 15% (w/w) peptide.

Poly(DTE carbonate) was also formulated with 15% (w/w) peptide. This polymer structure contains only the desaminotyrosyltyrosine ethyl ester with carbonate linkages and does not contain any PEG. These films also showed the same behavior as the tyrosine-derived polyarylates (FIG. 17). The water uptake of these films was also measured and found to be 6% by weight over the incubation period.

Figure 18:
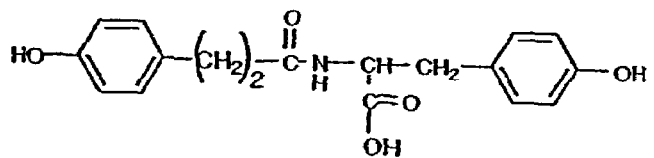
FIG. 18 depicts the chemical structure of desaminotyrosyltyrosine (DT)

Pulsatile Delivery of a Model Water Soluble Peptide Using Novel Synthetic Copolymers A monomer containing a free acid group randomly replaced the DTH monomer at particular molar concentrations. The particular monomer containing the free acid group is desaminotyrosyltyrosine (DT) (FIG. 18). Three sets of films from this terpolymer were prepared each set with a different molar concentration of DT. The first set was poly (DT$_{0.05}$-co-DTH$_{0.95}$ adipate), another was poly(DT$_{0.10}$-co-DTH0$_{.90}$ adipate), and the last was poly(DT$_{0.15}$-co-DTH$_{0.85}$ adipate). Since the DT content is the parameter that controls the rate of development of acidity within these polymers, the objective of these experiments was to observe the effect of increasing DT content of the polymer on the release of the peptide.

Degradation Mechanism of the Poly(DT-co-DTH Adipate) Polymers

The degradation of the tyrosine-derived polyarylates proceeds via an acid hydrolysis mechanism that is similar to the hydrolysis of poly(DTE carbonate). The pendent ester groups in contact with water would hydrolyze initially and the resulting acid groups would begin the hydrolysis of the backbone ester, liberating DTH and adipic acid. The adipic acid contributes to the acidity within the matrix and further promotes the hydrolysis of both backbone and pendent ester groups. However, it has been demonstrated that this is a relatively slow process, only 40% degradation occurs during a 2 month degradation period and the degradation rate begins to plateau after reaching this extent of degradation (FIG. 9).

The addition of DT to the polymer backbone accelerates the degradation process. The degradation rate is hastened because the hydrolyzed pendent ester is already present and randomly scattered throughout the polymer prepared for the random scission of the polymer chains. Moreover, since the degradation products of the terpolymer are more acidic than those of poly(DTH adipate) due to the increase in concentration of DT relative to DTH there is an autocatalytic effect similar to what has been observed with PLA/PGA derived polymers.

Figure 19:
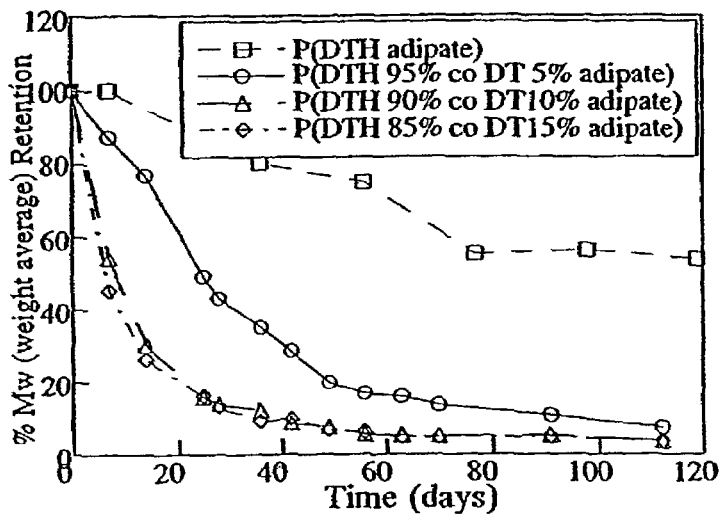
FIG. 19 depicts percent molecular weight retention of neat poly(DT-co-DTH adipate) films with 0, 5, 10, 15 mole percent of DT.

An investigation comparing the effect of increasing mole percent of DT on the degradation rate of poly(DTH adipate) was made (FIG. 19). It was observed that with the addition of anywhere between 5 and 15 mole percent DT the sample. films had chemically degraded by 90-95% within 3 months. These data indicate that DT does catalyze degradation, but it also indicates that there is a maximum limit to the catalytic effect of the DT. This is seen in the similarity in rate of degradation between the polymer containing 10 mole percent of DT and that with 15 mole percent of DT.

In addition, it can also be concluded from the percent molecular weight retention data that the autocatalytic effect is present in these polymers. This can be observed in the rate of degradation of the polymer with 5 mole percent DT. The rate of degradation begins much slower than the rate of degradation of the polymers with higher percentages of DT. However after 120 days the percent molecular weight retention is approximately the same as it is for the samples with higher DT content. This suggests that whatever initial acidity developed in the matrix of the polymer containing 5 mole percent DT resulted in the further increased hydrolysis of the pendant chain of the DTH repeat unit, converting the DTH repeat unit to the DT repeat unit. In this manner, the number of DT repeat units increased from the original 5 mole percent and consequently, the rate of degradation of this polymer increased until it was able to "catch up" with the rate of degradation of the polymers containing higher mole percentages of DT.

Water Uptake of Poly(DT-co-DTH Adipate) Films

Figure 20:
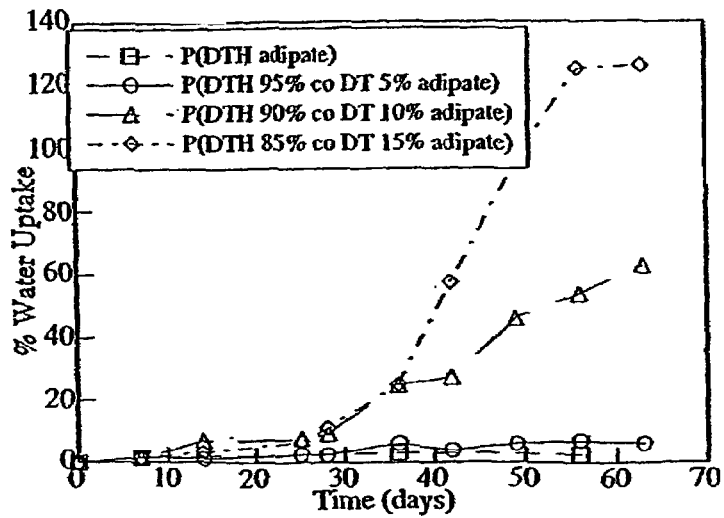
FIG. 20 depicts percent water uptake of neat poly(DT-co-DTH adipate) films with 0, 5, 10, and 15 mole percent DT.

In spite of the increased hydrophilicity of DT versus DTH there is no significant effect of mole percent of DT on amount of water absorbed by the polymer when samples are initially incubated (FIG. 20). Moreover significant water uptake does not appear to cause degradation, rather it seems to be an effect of the degradation. This can be observed by comparing the water uptake during the first two weeks of incubation. During these two weeks the rate of degradation is highest for the polymers containing 10 or 15 mole percent DT, yet this is also the period of time that is associated with the lowest percent water uptake. This is further observed by noting that the polymers that do absorb more than 20% water do not absorb this until they have degraded by 90%.

Visual Inspection of Poly(DT-co-DTH Adipate) Containing Peptide

The three types of terpolymers were formulated in the same technique as used for the copolymer, poly(DTH adipate), and two loadings of peptide were explored. One loading was 15% (w/w) peptide and the other 30% (w/w) peptide. Those films containing 15% (w/w) peptide were completely transparent, there was no difference between the neat copolymer films and films that contained 15% (w/w) peptide.

Samples from films that contained 30% (w/w) were slightly hazy. All of the polymers were flexible and easy to handle.

Analysis of Miscibility of Terpolymer Using DSC

Thermograms of these terpolymers indicated only one glass transition which was in the vicinity of the glass transition of poly(DTH adipate). The appearance of only one glass transition indicates there is a miscibility between the DTH adipate and the DT adipate, not surprising since they share a very similar structure. Moreover, the range of temperatures over which the glass transition occurs, is about 6° C. This is about the same for poly(DTH adipate) indicating that the polymer is quite homogeneous.

There was a trend of increasing $T_g$ with increasing mole percent of DT, this is quite expected since an increase in the amount of DT could result in an increase in hydrogen bonding between the chains and thereby increasing the rigidity of the polymer (Table 1). The homogeneity of the copolymer, in all probability, contributes to the transparency and clarity of those films that contain peptide.

TABLE 1

$T_g$ of poly (DT$_x$-co-DTH$_{1-x}$ adipate) x = 5, 10, 15

| Mole Percent DT in Polymer | $T_g$ (° C.) |
|---|---|
| 0 | 37 |
| 5 | 37 |
| 10 | 43 |
| 15 | 46 |

Peptide Release from Terpolymer Films Containing 15% (w/w) Loading

Figure 21:
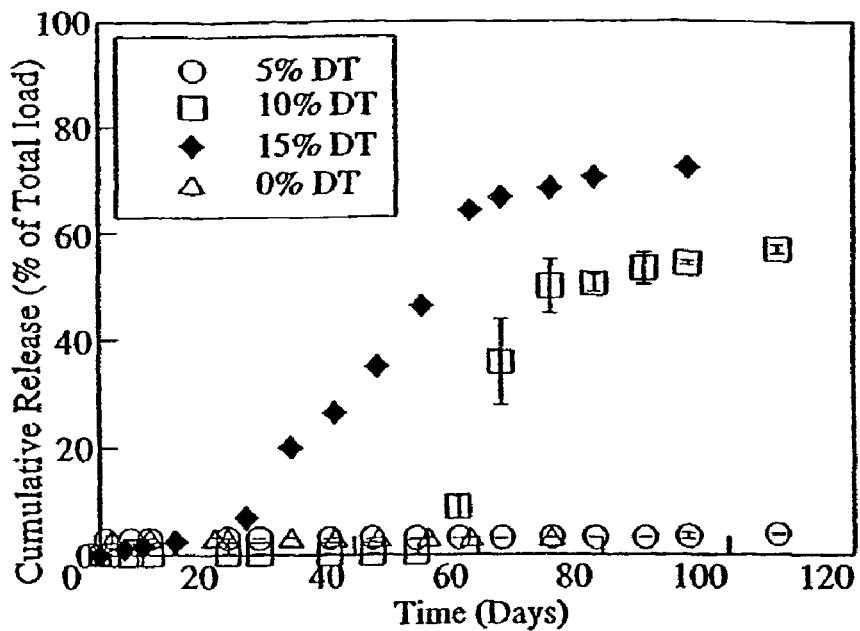
FIG. 21 depicts release of peptide from poly(DT-co-DTH adipate) matrices.

The incubation conditions were the same used in the above experiments. The results of these experiments were a delayed release, and the length of the delay time was a function of the mole percent of DT. The set of films containing 15 mole percent DT was characterized by a lag time of 20 days, after this lag time, 60% of the loaded peptide was released over a period of 40 days (FIG. 21). Samples containing 10% DT were associated with a lag time of close to 60 days. This delay period was followed by a release phase where 60% of the loaded peptide was released within 30 days. Samples with 5% DT never released the peptide even after 110 days of incubation. The control in this experiment was poly(DTH adipate) samples containing 15% (w/w) peptide which, also, did not release the peptide. In all samples no burst was observed and no leaching of the peptide occurred during the lag time.

The correlation of shorter lag time with increasing mole percent of DT is not unexpected. The samples containing larger mole percents of DT would be expected to accumulate acidic degradation products faster creating a higher concentration of these products in the bulk of the polymer resulting in the weakening of the peptide-polymer interactions earlier than those polymers with lower percentages of DT.

Peptide Release from Terpolymer Films Containing 30% (w/w) Peptide

Figure 22:
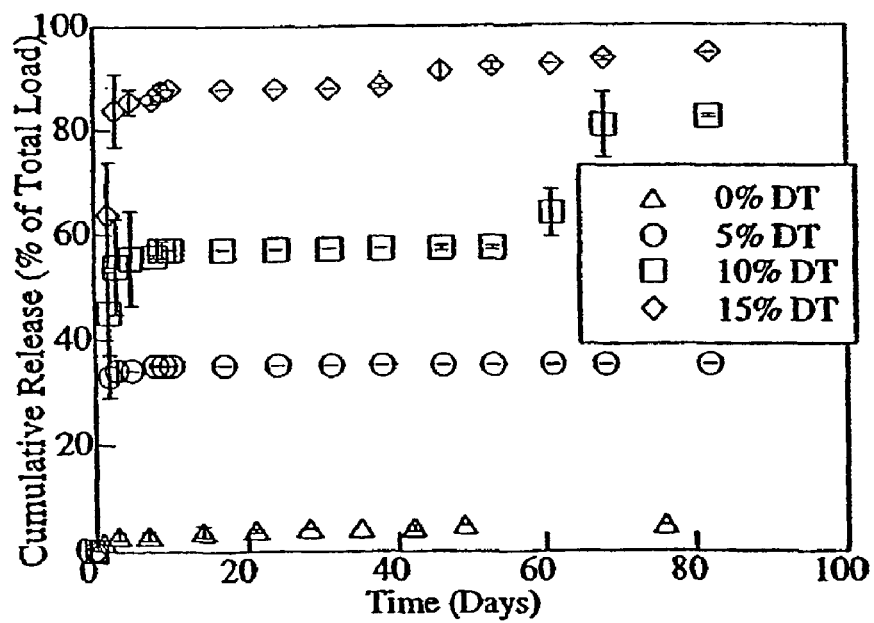
FIG. 22 depicts release of peptide from 30% (w/w) poly (DT-co-DTH adipate) films.

In contrast to the terpolymer samples containing 15% (w/w) peptide that were not characterized by a burst of peptide, these samples which contained 30% (w/w) all demonstrated large bursts (FIG. 22). The bursts were proportional to the mole percent of DT in the polymer. The reason for the large burst observed with the higher peptide loading could be the following: since the $pK_a$ of the tyrosine acid proton is approximately 2, it would be expected that when incubated initially, the majority of DT acid protons would be lost to the medium. Therefore, any peptide molecules that would be hydrogen bonded to this proton would no longer be interacting with this group once the proton is lost, and therefore these peptide molecules would be lost as a burst. In addition, after the loss of the acid proton, the carboxyl-ate group of the DT might actually compete with the peptide for interaction sites on the DTH repeat unit resulting in the release from the films of the peptide molecules that lost the competition. Furthermore, the higher the DT content in the polymer the more competition for the peptide and consequently, the size of the burst is correlated with increasing mole percent of DT. However following the initial changes that occur when the specimens are first incubated a new equilibrium is established of all the components, and no further release of peptide occurs for many days. This phenomenon is not observed with those terpolymer samples containing the lower loading of peptide because there are many fewer molecules of peptide and sufficient DTH sites for both the interaction of the peptide and the DT.

Samples containing 10% DT were also characterized by a second release phase. This second release phase occurred at approximately 60 days which is also when the release of the peptide was observed in samples of this polymer containing 15% (w/w) peptide. This release is due to the weakening of the interactions associated with the drop in pH of the polymer matrix. This polymer is quite unique among this grouping because these specimens alone can be considered a pulsatile release system. The films containing 15% DT also demonstrated a second release phase at about 40 days but it is much smaller than the second release phase of the specimens containing 10% DT. Samples with 5% DT, again, as in the 5% DT samples containing 15% (w/w) peptide, presumably, never reached the critical pH necessary for release of the peptide, and, therefore, following the burst no more peptide was released.

Figure 23:
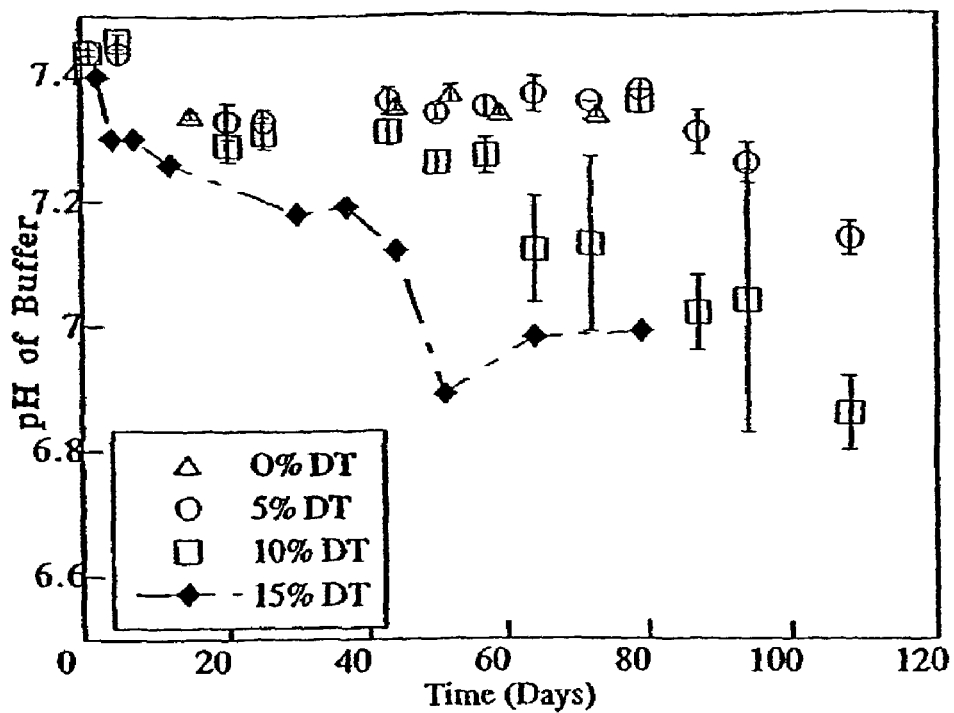
FIG. 23 depicts pH measurements of buffer of samples of poly(DT-co-DTH adipate) with 15% (w/w) peptide.

Analysis of the Buffer Media of the Poly(DT-co-DTH Adipate) Containing 15% (w/w) Peptide for pH Changes The buffer media were analyzed for pH changes at each buffer change (FIG. 23). Since the release of the peptide depends on the lowering of the pH of the matrix a detectable lowering of the pH should coincide with the release of the peptide. As expected, those films composed of the polymer system with 15 mole percent of DT demonstrated a drop of the pH below 7.2, first. This reduction in pH began at approximately 30 days which was 10 days after release of the peptide commenced. The pH of the media remained around 7.0 for the remainder of the incubation.

Samples containing 10 mole percent of DT were characterized by a drop in pH below 7.2 beginning around 60 days, which is precisely when release of the peptide commenced. The pH of the media of these samples remained approximately 7.0 for the remainder of the incubation period.

Specimens containing 5 mole percent of DT behaved exactly like the poly(DTH adipate) samples that did not contain any DT at all. Both types of samples remained between 7.3 and 7.4 for the first 100 days of the incubation. After this time both types of samples dropped to and remained at 7.2 for the remainder of the incubation period. The data indicate that there is a correlation between release of the peptide and generation of acidic degradation products. Specifically, only those samples that released peptide were associated with a drop in pH below 7.2 and this drop coincided with peptide release.

In addition, control samples of poly(DTH adipate) containing 15% (w/w) peptide were placed in buffer at a pH of 7.0. This again, was to observe whether environmental pH affects the release of the peptide. Trace release of the peptide was seen from these control samples. No difference in the behavior of these samples as compared to samples incubated in buffer at 7.4 was observed.

Chemical Integrity of the Released Peptide from Poly(DT-co-DTH Adiapte) Matrices The only polymer matrix of the group of polymers investigated in these experiments that released any of the peptide with the cleaved disulfide bond was the poly($DT_{0.15}$-co-$DTH_{0.85}$ adipate) samples which contained the lower loading of peptide. These samples began the release phase after a lag time of 20 days and continued this steady release until approximately 60 days of incubation. Intact peptide was released within the first 20 days of the release phase. However from the 44$^{th}$ day of incubation and beyond, fully one third of the peptide released was associated with a cleaved disulfide bond. Again, peptide with a cleaved disulfide bond was not observed in association with any other polymer system in these studies.

Figure 24:
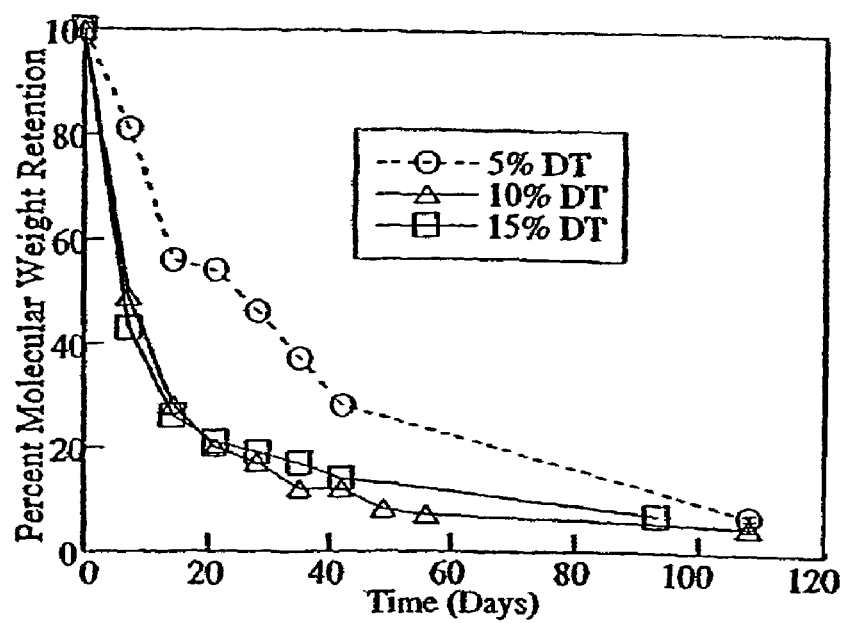
FIG. 24 depicts percent molecular weight retention of samples of poly(DTH adipate) containing various percentages of DT incubated in PBS at 37° C.

Percent Molecular Weight Retention During in vitro Incubation of Poly(DT-co-DTH Adipate) Samples Containing 15% (w/w) Peptide The percent molecular weight retention data of the various sets of films containing 15% (w/w) peptide were not significantly different than samples without peptide (FIGS. 24 and 19). This suggests that the catalytic degradation effect on the polymer of the DT is more important than the catalytic effect of the aspartic acid group of the peptide. In addition, although the polymer containing 15% DT released the peptide far earlier than the polymer with 10% DT the molecular weight degradation rate was the same. The explanation for this observation is that there is a sufficient number of DT repeat units in both polymer systems to reach the maximum rate of hydrolysis. However due to the increased amount of DT in the poly($DT_{0.15}$-co-$DTH_{0.85}$adipate) relative to the polymer with 10 mole percent DT, the degradation products also contain more DT and therefore critical concentration of acidic products necessary for release of the peptide is reached earlier with these samples than the polymers with 10 mole percent of DT.

Comparison of the Mechanism of Degradation of the Poly (DT-co-DTH Adipate) Samples with and without Peptide The poly(DT-co-DTH adipate) polymers without peptide appear to degrade through the same mechanism. The rates may be different especially between those polymers that contain 5 mole percent of DT and those that contain more DT but the end result appears similar. After 16 weeks of incubation the polymers have all developed a significant amount of low molecular weight fractions and there does not appear to be a preference for the formation of one particular fraction over another.

In contrast, the samples that were formulated with peptide do not all degrade by the same mechanism. Samples with 5 mole percent DT behave similarly to the neat samples; there is the random scission of the chains forming a variety of oligomers and no special preference for the formation of a specific degradation product is observed in the GPC chromatograms of the degraded samples. This observed behavior was consistent for this polymer system whether it was loaded with 15% (w/w) peptide, 30% (w/w) peptide or neat.

However, those films of poly($DT_{0.10}$-co-$DTH_{0.90}$ adipate) containing peptide (it was the same for both loadings of peptide) exhibited a distinct preference for the formation of monomer during the degradation process. The monomer (DTH) has a retention time of 18.6 minutes in the GPC and starting from the 5$^{th}$ week of incubation and beyond there is the presence of a well defined peak at this retention time in the chromatograms of these samples. This implies that the polymer degrades in the random scission manner until it reaches about 20% molecular weight retention at five weeks of incubation. After this point the polymer begins to degrade in an unzipping process. This unzipping process means that the degradation begins from the chain ends and moves in along the chain. Consequently, each scission results in the formation of monomer. The poly($DT_{0.15}$-co-$DTH_{0.85}$ adipate) samples that contain peptide exhibited this same behavior as described for the poly($DT_{0.10}$-co-$DTH_{0.90}$ adipate) samples that contain peptide.

Physical Disintegration During in vitro Incubation of Samples of Poly(DT-co-DTH Adipate) Samples Containing Peptide There were no significant physical changes in these samples for the first two weeks of incubation. However, by the third week all the samples have become opaque, and by the fourth week there was significant shredding of the samples containing 15% DT. In fact, so much shredding has occurred that the buffer media has turned opaque. No significant shredding of the samples containing 10% DT occurred before 70 days and the samples containing 5% DT never shredded at all.

This shredding is most likely related to the dissolution of the water soluble degradation products of the polymers. Both polymers with the higher free acid content contain a significant amount of water soluble degradation products (DT and adipic acid) and therefore shredding is common to both of them. Since shredding occurs in both of these polymer systems the resulting films following incubation of 80 or more days appeared transparent with only a "skin" of the material left. All of the bulk had disappeared. Shredding never occurs in the polymer with the lower free acid content since it never develops enough water soluble components within the bulk and therefore, though, these samples swelled and curled during the incubation period they remained smooth and intact. The same phenomena was observed with the poly(DT co-DTH adipate) samples containing 30% (w/w) peptide.

The foregoing illustrates that polymers that form hydrolytic degradation products promote the release of biologically active compounds from the polymer matrix in comparison to polymers of similar structure that do not hydrolytically degrade. Neither polymer initially releases the biologically active compound. However, a delayed pulsatile release is obtained from polymers that hydrolytically degrade as the degradation products accumulate, while significant quantities of biologically active compound are never released from the polymers that do not hydrolytically degrade.

The foregoing examples and description of the preferred embodiment should be taken as illustrating, rather than as limiting, the present invention as defined by the claims. As will be readily appreciated, numerous variations and combinations of the features set forth above can be utilized without departing from the present invention as set forth in the claims. Such variations are not to be regarded as a departure from the spirit and scope of the invention, and all such modifications are intended to be included within the scope of the following claims.

What is claimed is:

1. A method for preparing a delayed-release formulation which comprises combining:
   a) a weight percentage of a biologically active compound having a chemical structure with hydrogen bonding sites, and
   b) a biocompatible, hydrolytically degradable polyarylate copolymer comprising tyrosine-derived diphenol monomer units with pendant carboxylic acid groups and tyrosine-derived diphenol monomer units with pendant carboxylic acid ester groups, said copolymer having a mole percentage of the monomer units with pendant carboxylic acid groups, to produce said formulation,
   wherein the weight percentage of the biologically active compound in the formulation relative to the mole percent of the monomer units with pendant carboxylic acid groups in the copolymer is effective to provide reproducible release profiles of the biologically active compound from the formulation under physiological conditions with a time lag inversely proportional to the mole percent of the monomer units with pendant carboxylic acid groups and without leaching the biologically active compound during the lag time.

2. The method of claim 1, wherein release of said compound is delayed at least 20 days.

3. The method of claim 1, wherein release of said compound is delayed at least 60 days.

4. The method of claim 1, wherein the mole percent of the monomer units with pendant carboxylic acid groups in the copolymer is 10% to 15%.

5. The method of claim 1, wherein said compound is a peptide or a protein.

6. The method of claim 1, wherein said compound is an antibiotic.

7. The method of claim 1, wherein said compound is a cytotoxic agent.

8. The method of claim 1, wherein said compound is a hormone.

9. A delayed release formulation prepared by the method of any one of claims 1-8.

10. A method for preparing a biphasic release formulation which comprises combining:
    a) a weight percentage of a biologically active compound having a chemical structure with hydrogen bonding sites, and
    b) a biocompatible, hydrolytically degradable polyarylate copolymer comprising tyrosine-derived diphenol monomer units with pendant carboxylic acid groups and tyrosine-derived diphenol monomer units with pendant carboxylic acid ester groups, said copolymer having a mole percentage of the monomer units with pendant carboxylic acid groups, to produce said formulation,
    wherein the weight percentage of the biologically active compound in the formulation relative to the mole percent of the monomer units with pendant carboxylic acid groups in the copolymer is effective to provide reproducible release profiles of the biologically active compound from the formulation under physiological conditions with an initial burst release followed by a delayed release.

11. The method of claim 10, wherein the delayed release occurs after about 40 days.

12. The method of claim 10, wherein the delayed release occurs after about 60 days.

13. The method of claim 10, wherein the mole percent of the monomer units with pendant carboxylic acid groups in the copolymer is 10% to 15%.

14. The method of claim 10, wherein said compound is a peptide or a protein.

15. The method of claim 10, wherein said compound is an antibiotic.

16. The method of claim 10, wherein said compound is a cytotoxic agent.

17. The method of claim 10, wherein said compound is a hormone.

18. A delayed release formulation prepared by the method of any one of claims 10-17.

19. A formulation for the delayed release of biologically active compounds, said formulation comprising:
    a) 15 wt % of a biologically active compound having a chemical structure with hydrogen bonding sites, and b) a biocompatible, hydrolytically degradable polyarylate copolymer comprising (i) from 10 mol% to 15 mol% of tyrosine-derived diphenol monomer units with pendant carboxylic acid groups and (ii) tyrosine-derived diphenol monomer units with pendant carboxylic acid ester groups, wherein the release of said biologically active compound from the polyarylate copolymer is delayed at least 20 days.

20. A formulation for the delayed release of biologically active compounds, said formulation comprising:

a) about 30 wt % of a biologically active compound having a chemical structure with hydrogen bonding sites, and b) a biocompatible, hydrolytically degradable polyarylate copolymer comprising (i) from about 10 mol % to about 15 mol % of tyrosine-derived diphenol monomer units with pendant carboxylic acid groups and (ii) tyrosine-derived diphenol monomer units with pendant carboxylic acid ester groups, wherein the release of said biologically active compound from the polyarylate copolymer is as an initial burst release followed by a second release after at least about 40 days.

* * * * *